United States Patent
Harding et al.

(10) Patent No.: US 9,101,748 B2
(45) Date of Patent: Aug. 11, 2015

(54) PUSH-BUTTON BLOOD CONTROL

(75) Inventors: Weston F. Harding, Lehi, UT (US);
Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1817 days.

(21) Appl. No.: 12/117,525

(22) Filed: May 8, 2008

(65) Prior Publication Data
US 2009/0281525 A1 Nov. 12, 2009

(51) Int. Cl.
*A61M 39/06* (2006.01)

(52) U.S. Cl.
CPC ....... *A61M 39/0613* (2013.01); *A61M 39/0693* (2013.01); *A61M 39/06* (2013.01); *A61M 2039/062* (2013.01); *A61M 2039/064* (2013.01); *A61M 2039/0673* (2013.01)

(58) Field of Classification Search
CPC ..... A61M 39/22; A61M 2039/1072; A61M 39/06; A61M 39/0613; A61M 2039/066; A61M 2039/2426; A61M 2039/2433; A61M 2039/0036; A61M 39/0606; A61M 2039/062; A61M 2039/064; A61M 2039/0633; A61M 2039/0673; A61M 39/0693
USPC ............... 604/167.01–167.05, 246, 250, 256, 604/537, 539
See application file for complete search history.

(56) References Cited

U.S. PATENT DOCUMENTS

| | | | |
|---|---|---|---|
| 3,811,440 A * | 5/1974 | Moorehead et al. ..... | 604/167.01 |
| 3,856,010 A | 12/1974 | Moorehead et al. | |
| 3,895,632 A | 7/1975 | Plowiecki | |
| 3,977,400 A | 8/1976 | Moorehead | |
| 4,381,778 A * | 5/1983 | Kozam et al. ............... | 604/191 |
| 4,387,879 A | 6/1983 | Tauschinski | |
| 4,449,693 A | 5/1984 | Gereg | |
| 4,662,871 A * | 5/1987 | Rafelson ................ | 604/119 |
| 4,758,225 A | 7/1988 | Cox et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 5,041,097 A | 8/1991 | Johnson | |
| 5,053,014 A | 10/1991 | Van Heugten | |
| 5,061,253 A | 10/1991 | Yoshida | |
| 5,062,836 A | 11/1991 | Wendell | |
| 5,064,416 A | 11/1991 | Newgard et al. | |
| 5,071,411 A | 12/1991 | Hillstead | |
| 5,084,023 A | 1/1992 | Lemieux | |
| 5,085,645 A | 2/1992 | Purdy et al. | |
| 5,098,394 A | 3/1992 | Luther | |
| 5,108,374 A | 4/1992 | Lemieux | |
| 5,108,380 A | 4/1992 | Herlitze et al. | |

(Continued)

FOREIGN PATENT DOCUMENTS

| CA | 2133053 A1 | 3/1995 |
|---|---|---|
| WO | 95/15779 | 6/1995 |

(Continued)

*Primary Examiner* — Aarti B Berdichevsky
*Assistant Examiner* — Laura Schell
(74) *Attorney, Agent, or Firm* — Jeanne Lukasavage; Craig Metcalf; Kirton McConkie

(57) ABSTRACT

A device for controlling fluid flow through an indwelling catheter assembly. The device includes a septum that is closed by default but that may be defeated temporarily by either exerting a force on a contact surface of the septum, or by biasing the septum with a probe.

18 Claims, 16 Drawing Sheets

(56) References Cited

U.S. PATENT DOCUMENTS

| | | |
|---|---|---|
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,380,305 A | 1/1995 | Ghouri |
| 5,405,323 A | 4/1995 | Rogers et al. |
| 5,429,616 A | 7/1995 | Schaffer |
| 5,456,675 A | 10/1995 | Wolbring et al. |
| 5,487,728 A | 1/1996 | Vaillancourt |
| 5,514,114 A | 5/1996 | Soto-Tolosa et al. |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,857 A | 5/1998 | Cuppy |
| 5,749,861 A | 5/1998 | Guala et al. |
| 5,782,816 A | 7/1998 | Werschmidt et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2004/0044313 A1 | 3/2004 | Nakajima |
| 2004/0082923 A1* | 4/2004 | Field ............................ 604/267 |
| 2005/0043684 A1* | 2/2005 | Basta et al. ............. 604/164.13 |
| 2006/0155245 A1 | 7/2006 | Woehr |
| 2007/0083162 A1 | 4/2007 | O'Reagan et al. |
| 2008/0039796 A1 | 2/2008 | Nakajima |
| 2008/0108944 A1 | 5/2008 | Woehr et al. |
| 2010/0204675 A1 | 8/2010 | Woehr et al. |

FOREIGN PATENT DOCUMENTS

| | | |
|---|---|---|
| WO | WO 99/34849 | 7/1999 |
| WO | 02/096495 A2 | 12/2002 |

* cited by examiner

PUSH-BUTTON BLOOD CONTROL

BACKGROUND OF THE INVENTION

The present disclosure relates generally to infusion therapy practice and procedures. Specifically the present disclosure relates to an indwelling catheter assembly for use in artificial dialysis, fluid infusion, or blood infusion, and more particularly to an indwelling catheter assembly which provides flow control for a fluid passing through the catheter assembly.

Typically, catheter assemblies comprise a catheter adapter and a catheter wherein a lumen of the catheter adapter and a lumen of the catheter are in fluid communication. Upon insertion of the catheter into the vasculature of a patient, the blood of the patient flow freely though the catheter and into the lumen of the catheter adapter. This blood flow is termed "flashback" and is desirable to ensure proper insertion of the catheter. To prevent undesirable exposure to the blood, a clinician will typically control the blood flow through the catheter assembly by occluding the catheterized vein of the patient. Occlusion may be accomplished either by applying a constricting band or pressure cuff to the catheterized vein, or by restricting the flow through the vein by applying pressure directly to the catheterized vein with the clinician's finger or fingers.

Use of a constricting band or pressure cuff is undesirable due to the difficulty associated with monitoring flashback through the catheter assembly. For example, where a constricting band or pressure cuff is used, a clinician must first constrict the patient's vein prior to insertion of the catheter. As the catheter is inserted into the patient, the constricting band prevents flashback and therefore the clinician has no clear indicator as to the proper positioning of the catheter. Flashback is only available when the clinician releases the constricting band thereby no longer occluding the vein. If the catheter is placed incorrectly, the clinician must once again set the constricting band or pressure cuff and reattempt insertion. Aside from requiring additional equipment, the use of a constricting band or pressure cuff is time consuming and inefficient for catheterization.

Occluding the patient's vein with the clinician's finger or fingers is similarly constraining and inefficient. Following insertion of the catheter into the vein of the patient, a clinician must quickly occlude the vein by applying pressure on the catheterized vein at a location upstream from the insertion site. The clinician may control the flow of blood through the catheter assembly by releasing or applying pressure to the catheterized vein. However, the clinician must maintain contact with the patient or the blood will flow uncontrollably from the catheter assembly and create a risk of undesirable exposure. Therefore, if the clinician chooses to occlude the vein in this manner, the clinician is restricted to only one free hand with which to provide additional medical care to the patient until the catheter is further connected to an infusion system or clamped.

Following catheterization a clinician may also desire to collect a blood sample. Typically this can be accomplished by one of two methods. Firstly, the clinician may attach a vacuum tube or collection vial to the end of the catheter adapter and draw blood from the patient. In some cases, the negative pressure of the vacuum collection vial causes the patient's catheterized vein to collapse. Collapsing the patient's vein requires that the clinician locate a new vein and reinsert the catheter. Additionally, collapsing the vein may damage the vein of the patient as well as cause bruising and tenderness to the patient.

Secondly, the clinician may allow the blood to flow freely from the catheter adapter and collect the patient's blood in a collection vial. This method of collection does not expose the patient's vein to possible collapse, but does require that the clinician control the blood flow either with a constriction band or by applying pressure to the patient's vein with the clinician's finger or fingers. This method of collection is also undesirable due to the clinician's need to use both hands in collecting, labeling and storing the blood samples.

Thus, there exists a need for a catheter assembly with integrated flow control capabilities. Specifically, a need exists for a catheter assembly that allows a clinician to control blood flow through the catheter assembly without the need of occluding the patient's vein with additional equipment or the clinician's fingers.

BRIEF SUMMARY OF THE INVENTION

The systems and methods of the present disclosure have been developed in response to problems and needs in the art that have not yet been fully resolved by the currently available catheter assemblies. Thus, these systems and methods are developed to provide for a more efficient catheter assembly and infusion system.

One aspect of the present disclosure provides a catheter assembly. The catheter assembly may comprise a catheter adapter and a catheter. The catheter adapter body may comprise a generally rigid or semi-rigid material such as a polymer material. In one embodiment the catheter adapter comprises a rigid polymer material while in another embodiment the catheter adapter comprises a semi-rigid material. A proximal end of the catheter adapter may also be modified to include a feature for attaching a component of an infusion system.

The catheter assembly may also comprise an opening or window in the surface of the catheter adapter body. The window may be provided to allow a flow control button to be accessed by a user of the catheter assembly. The flow control button may be provided adjacent to a valve or septum of the catheter assembly whereby a user may depress the flow control button to actuate the valve or a septum within the catheter adapter body.

The catheter of catheter assembly is generally tubular and comprises a flexible or semi-flexible material. The catheter may comprise a polymer material such as polypropylene, silicon or Teflon. In one embodiment, the catheter comprises a silicon material. The catheter forms a junction with the catheter adapter such that the lumen of the catheter and the lumen of the catheter adapter are in fluid communication. The catheter assembly may also incorporate an introducer needle to assist a user in inserting the catheter into the vasculature of a patient. The introducer needle may be slidably housed within the lumen of the catheter such that a tip of the introducer needle extends beyond a tip of the catheter. A user may then pierce the skin of the patient with the tip of the introducer needle and advance the introducer needle and catheter into the vasculature of the patient.

The catheter assembly further includes a valve or septum deposited within the lumen of the catheter adapter body. The septum generally comprises a flexible or semi-flexible material. The septum may comprise a polymer material such as polypropylene, silicon or Teflon. In one embodiment, the catheter is a silicon material.

The septum may also include a slit or opening through which a fluid may pass. The septum further comprises an inner membrane comprising a first half and a second half. The first and second halves of the inner membrane further comprise an interface surface. The first and second halves of the inner membrane are biased inwardly such that the interface surface forms a fluidtight seal thereby preventing a fluid from passing through the septum of the catheter assembly. In this manner, the catheter assembly is divided into a first compartment and a second compartment, the compartments being separated by the inner membrane of the septum.

By default, the septum is in a closed state. Therefore, by default, a fluid is unable to pass or flow through the slit or opening of the septum. As such, a clinician may insert the catheter into a patient, remove an introducer needle from the catheter assembly and the blood of the patient is prevented from flowing through the catheter assembly. Once the catheter is inserted, the clinician may defeat or actuate the septum of the catheter adapter to allow blood to flow through the catheter assembly. The septum may be actuated either by applying pressure to an outer surface of the septum, or by inserting a probe through the inner membrane of the septum.

The septum may be actuated or opened by depressing an adjacently located flow control button. In one embodiment, the flow control button is an outwardly extended portion of the septum. This outwardly extended portion of the septum extends through the surface of the catheter adapter via the provided window. In this manner a user may depress the septum by contacting and depressing the flow control button. The flow control button is positioned so as to be centered over the inner membrane of the septum. As the flow control button is depressed, the downward force of the flow control button is directly transferred to the inner membrane of the septum. As such, the first and second halves of the inner membrane are biased outwardly thereby disrupting the interface between the two halves. The resultant disruption of the interface reveals a pathway through the septum by way of the separated halves of the inner membrane.

Alternatively, the septum may be actuated by inserting a probe into an opening of the catheter assembly, located at the proximal end of the catheter adapter body. In one embodiment, the septum is actuated as the probe is inserted through the lumen of the of the catheter adapter and advanced through the inner membrane of the septum. As such, the tip of the probe outwardly biases the first and second halves of the inner membrane thereby providing a pathway through the inner membrane. In another embodiment, an actuator is positioned within a docking portion of the septum at a location proximal to the inner membrane. In this embodiment the septum is actuated as the tip of the probe contacts a proximal end of the actuator and advances the actuator through the inner membrane of the septum. In this manner, the tip of the actuator outwardly biases the first and second halves of the inner membrane thereby providing a pathway through the inner membrane.

The catheter adapter body may also comprise a rigid or semi-rigid material that functions as an exoskeleton-like covering for an encased flexible or semi-flexible septum. In this embodiment, the catheter adapter body comprises one or more windows through which a use may directly contact the outer surface of the septum. The one or more windows are positioned so as to be adjacent to a middle portion of the septum. The middle portion of the septum further comprises an inner membrane, as previously discussed. The septum is actuated as the user depressed the outer surface of the septum via the one or more windows. Likewise, the septum may be actuated by advancing a probe through the proximal opening of the catheter assembly, as previously discussed.

The catheter assembly may also comprise a solid or impermeable septum. In one embodiment the septum does not comprise an inner membrane and does not comprise a pathway through the septum. Rather, the septum is generally impermeable and positioned within the lumen of the catheter adapter body so as to form an interface between the septum and the inner surface of the catheter adapter body. The interface between the septum and the catheter adapter body is fluidtight. As such, a fluid is prevented from flowing through the catheter assembly. The embodiment further comprises a flow control button. In this embodiment the flow control button comprises a contact surface coupled to a shaft. The shaft extends through the surface of the catheter adapter body and contacts the outer surface of the septum at a location distal to the interface between the septum and the inner surface of the catheter adapter body. The septum is actuated by one of two methods. Firstly, the septum may be actuated by depressing the flow control button. As the flow control button is depressed, the shaft of the button contacts and displaces the septum. The displaced septum disrupts the interface between the septum and the inner surface of the catheter adapter. As such, a pathway is provided through the catheter assembly, the pathway comprising the gap between the outer surface of the septum and the inner surface of the catheter adapter body.

Secondly, the septum may be actuated by advancing a probe through the proximal opening of the catheter adapter and contacting an outer surface of the septum. In this manner, the probe may compress the proximal end of the septum thereby disrupting the interface between the outer surface of the septum and the inner surface of the catheter adapter body. As such, a pathway is provided between the outer surface of the septum and the inner surface of the catheter adapter body.

The septum is further configured to include a plurality of flow channels. As such, a fluid may bypass the remainder of the septum following disruption of the interface, as previously described. A proximal end of the septum further comprises a plurality of flow channels such that a probe may contact the proximal end of the septum without forming a fluidtight interface between the outer surface of the septum and the tip of the probe. As such, a probe may actuate the septum, as described above, and then introduce a fluid into, or withdrawal a fluid from the lumen of the catheter adapter body.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
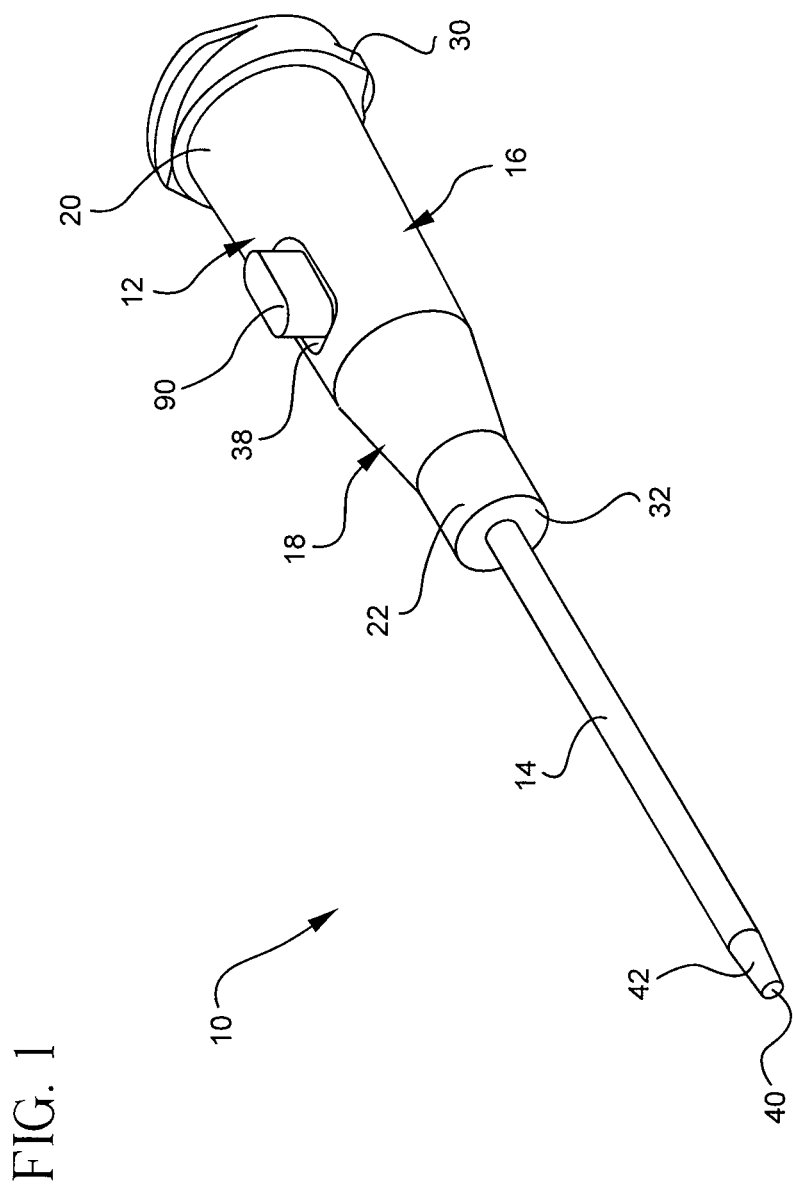
FIG. 1 is a perspective view of a catheter assembly with a flow control button.

Referring now to FIG. 1, a catheter assembly 10 is illustrated. The catheter assembly 10 includes a catheter adapter 12 and a catheter 14. The catheter adapter 12 includes a generally tubular body 16. The catheter adapter body 16 is generally comprised of a rigid or semi-rigid polymer material, such as polystyrene or polypropylene.

The catheter adapter body 16 further comprises a proximal end 20 and a distal end 22. The proximal end 20 may comprise a system of threads 30 or another system for attaching the proximal end 20 of the catheter assembly 10 to an additional component of an infusion system. For example, the threads 30 of the proximal end 20 may be used to attach the catheter assembly to section of intravenous catheter tubing comprising a complementary system of threads. Alternatively, the proximal end 20 may include an annular ridge over which a clip may engage to interlock the catheter assembly 10 and another component of an infusion system.

The distal end of the catheter adapter body 16 may include a tapered section 18. The tapered section 18 may be desirable for reducing the outer diameter of the catheter adapter 12 near the junction 32 of the catheter adapter 16 and the catheter 14. The tapered section 18 may also enable a desired angle of insertion for the catheter 14. For example, during insertion of the catheter 14, a clinician will generally insert the catheter 14 through the patient's skin and into the patient's vein at an angle greater than 15°. After the catheter 14 is advanced into the patient's vein, and the introducer needle is removed from the catheter 14, the clinician then supports the catheter adapter 12 on the external surface of the patient in a plane generally parallel to the external surface of the patient. As inserted, the catheter 14 is required to arch or bend to complete the transition between the angle of insertion and the final parallel orientation of the catheter adapter 12. In this final configuration, the arched portion of the catheter 14 may become partially kinked or occluded near the junction 32 of the catheter adapter 12 and the catheter 14. By providing a tapered section 18 on the catheter adapter body 16, the distance between the junction 32 and the patient's external surface may be reduced. As such, the degree to which the catheter 14 must arch is reduced thereby reducing the likelihood of occluding the catheter 14 near the junction 32.

The catheter adapter body 16 may also include a window 38. The window 38 may comprise an opening in the surface of the catheter adapter body 16 and may provide an opening to house a flow control button 90. The flow control button 90 will be discussed in greater detail below in connection with FIGS. 2-12a. The window 38 may further comprise a system for sealing the window against fluids within the catheter adapter 12. For example, a gasket or sealant may be incorporated between the window 38 and the flow control button 90 such that a fluid is prevented from penetrating the interface of the window 38 and the button 90. The flow control button 90 may also form a part of the catheter adapter body 16. As so configured, a fluid within the catheter adapter 12 will be contained within the catheter adapter body 16.

A junction 32 is formed where the catheter 14 extends from the distal end 22 of the catheter adapter 12. The catheter comprises flexible or semi-flexible tubing that may be inserted into a vein of a patient. Generally a catheter 14 is comprised of a polymer material such as polypropylene, silicon, or Teflon. The catheter 14 is generally tubular with an inner lumen configured to permit the passing of an introducer needle. An introducer needle is commonly used to aid a clinician in introducing the catheter into the vein of a patient. For example, an introducer needle may be inserted through the lumen of the catheter wherein a tip of the introducer needle extends beyond the tip portion 40 of the catheter 14. A tapered portion 42 of the catheter tip portion 40 may be configured to reduce the inner diameter of the catheter 14. As such, the tapered portion 42 of the catheter 14 may contact the outer surface of the introducer needle tip. In this way the introducer needle may pierce the skin of the patient and the tapered portion 42 of the catheter 14 may be inserted into the patient through the opening created by the introducer needle. Use of an introducer needle and catheter in this manner is common in the field of infusion therapy.

Figure 2:
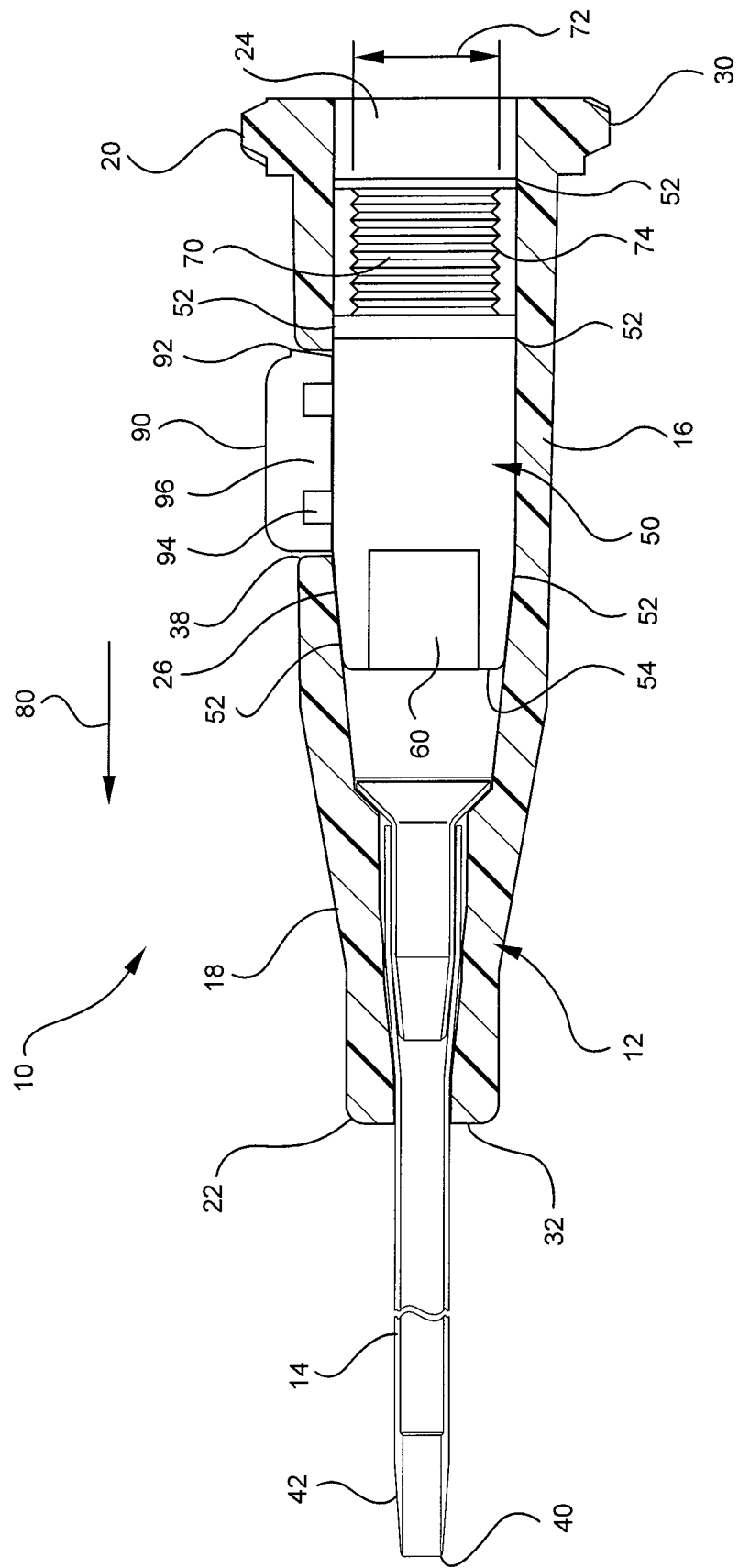
FIG. 2 is a cross-sectional side view of the catheter assembly of FIG. 1 in a closed state.

Referring now to FIG. 2, the catheter assembly 10 of FIG. 1 is illustrated in cross-sectional side view. As previously discussed, the catheter adapter body 16 may include a window 38 for providing an opening to house a flow control button 90. The flow control button 90 may comprise an extended portion of a valve member or a septum member 50. The septum member 50 is generally deposited within the lumen 24 of the catheter adapter body 16. The primary function of the septum member 50 is to control the flow of a fluid from the lumen 44 of the catheter 14 through the lumen 24 of the catheter adapter 12. The design of both the septum 50 and the flow control button 90 may be adapted to control the flow of a fluid through the catheter assembly 10.

For example, a user may apply pressure to the flow control button 90 and thereby apply pressure to the septum 50 within the lumen 24 of the catheter adapter 16. The flow control button 90 may be modified to include a system of channels 94 comprising the width of the button 90 and located between the button 90 and the septum 50. The channels 94 may be formed by removing a portion of the material of the button 90 such that the channels 94 are formed perpendicular to the length of the button 90. By removing a portion of the button 90 material, the force of the button 90 may be focused towards the middle section 96 of the button 90. As such, the channels 94 allow a user to apply pressure to a focused portion of the septum 50 by generally depressing the button 90. As will be described in detail below, the focused force of the button allows for the proper and accurate opening of a slit 60 through the septum 50.

The button 90 may be further modified to include a button catch 92. The button catch 92 comprises a wedged extension of the button whereby the button catch 92 is configured to interact with an edge of the window 38 of the catheter adapter 12. For example, a user may depress the button 90 such that the button catch 92 passes to the inside of the window 38 opening. As such, the button catch 92 may engage the inner surface 26 of the catheter adapter 12 and prevent the button 90 from returning to a released position. In this manner, the button 90 may continue to be depressed without requiring contact by the user. The button catch 92 may be disengaged from the inner surface 26 of the catheter adapter 12 by simultaneously depressing the button and biasing the button in a forward direction 80. The flexibility of the button 90 thereby permits the button to advance forward 80 to allow the button catch 92 to disengage and return through the window 38 opening to a released position.

The septum 50 and the flow control button 90 may be configured to control blood flow during insertion of the catheter 14 into a patient. Typically an insertion needle is used to aid the insertion of a catheter 14. Following insertion of the catheter tip 40 into the vein of the patient, the introducer needle is withdrawn from the catheter 14 and removed from the catheter assembly 10. At this point the pressure of the patient's vascular system will force the blood of the patient to travel up through the catheter 14. The septum 50 may be designed to include an interface 52 with the inner surface 26 of the catheter adapter 12 such that a fluidtight interface 52 is created. Therefore, a fluid, such as the blood of the patient, may be prevented from flowing past a first end 54 of the septum 50. The interface 52 may include a pressure fitting, an o-ring, a gasket or a portion of the septum 50. The interface 52 may also prevent a fluid from leaking through the window 38 of the catheter adapter. This is accomplished by configuring the interface 52 to sufficiently contact the inner surface 26 of the catheter adapter 12 thereby preventing passage of a fluid between the septum 50 and the inner surface 26 of the catheter adapter 12.

The septum 50 may be further modified to comprise a slit 60 thereby providing a pathway through the septum 50. The dimensions of the slit 60 may vary depending upon the needs of the catheter assembly 10. For example, where the catheter assembly 10 is used for high pressure or high volume infusions, it may be desirable to provide a larger slit 60 to compensate for the anticipated larger volume of infusate. The slit 60 may be included in the septum 50 by any method. For example, the slit 60 may be added to the septum 50 by slicing the septum 50 during manufacturing. Furthermore, the septum 50 and the slit 60 may be designed such that the slit 60 is biased in a closed state. The slit 60 may be biased open by depressing the flow control button 90, as discussed in greater detail below.

The septum 50 may further include a docking portion 70 located within the proximal end 20 of the catheter adapter 12. The docking portion 70 comprises a lateral extension of the septum 50 with an inner diameter 72 sufficient to receive a probe. As configured, a user may insert a probe into the lumen 24 of the proximal end 20 of the catheter adapter 12 and into the docking portion 70 of the septum 50. Once inserted, the user may advance the probe in a forward direction 80 thereby advancing the probe through the slit 60 of the septum 50. As the probe is advanced through the slit 60 of the septum 50, the slit 60 is biased open thereby providing fluid communication between the lumen 44 of the catheter 14, the lumen 24 of the catheter adapter 16 and the inserted probe. Upon removal of the probe, the slit 60 of the septum 50 returns to its closed state thereby preventing a fluid from flowing through the septum 50.

A probe may include any device capable of being inserted into the docking portion 70 of the septum 50 for biasing open the slit 60 of the septum 50. For example, the probe may include a Luer, a section of intravenous tubing, a needle, a blunt cannula or a stylus. Where the probe is a section of intravenous tubing, the inserted intravenous tubing biases open the slit 60 of the septum 50 thereby opening a pathway through the septum 50 for passage of a fluid. Once inserted, a fluid may be infused from the section of intravenous tubing into the patient, or a fluid, such as blood, may be withdrawn from the patient via the intravenous tubing.

The docking portion 70 may further include a ribbed section 74. The ribbed section 74 comprises a series of raised, annular ridges circumscribing the inner and outer surfaces of the docking portion 70. The ribbed section 74 permits the docking portion 70 of the septum 50 to be compressed in a forward direction 80 as a probe is inserted. Where the probe comprises a tapered outer surface, a portion of the probe may contact the ribbed section 74 during insertion of the probe. As such, the tapered, outer surface of the probe may bind on the ribbed section 74 of the septum and advance the ribbed section 74 in a forward direction 80. The raised, annular ridges of the ribbed section 74 permit the ribbed section 74 to compress in an accordion-like fashion thereby permitting continued insertion of the probe. The compressed position of the ribbed section 74 is maintained by the inserted probe. The probe is retained within the lumen 24 of the catheter adapter 12 via friction between the outer surface of the probe and the inner surface 26 of the catheter adapter 12. Upon removal of the probe, the compressed ribbed section 74 is returned to its original, unfolded configuration. In one embodiment, the compressed ribbed section 74 exerts a recoil force on the inserted probe. As such, the negative force required to remove the inserted probe is reduced due to the positive recoil force of the compressed ribbed section 74.

Figure 3:
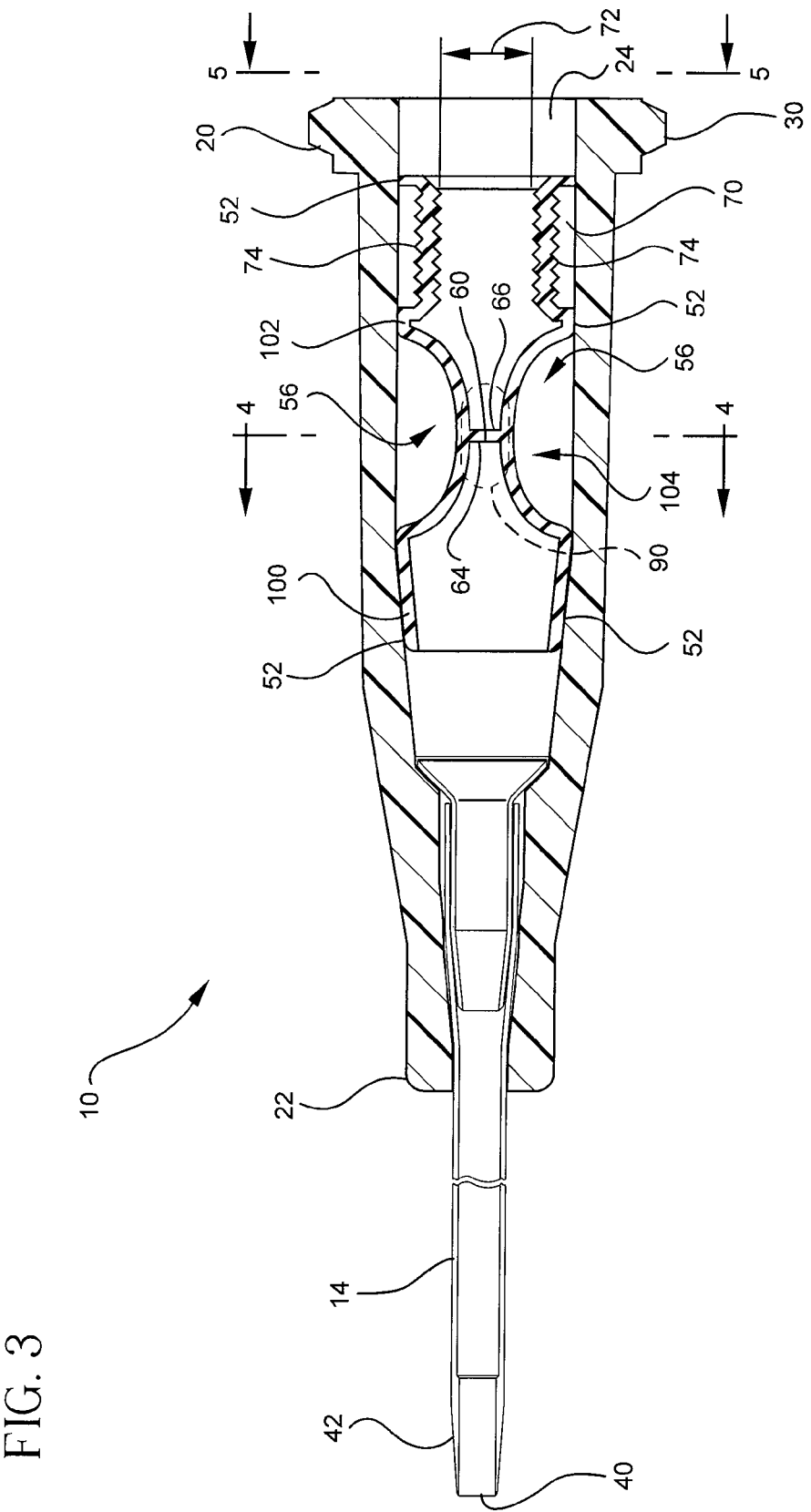
FIG. 3 is a cross-sectional top view of the catheter assembly of FIG. 1 in a closed state.

Referring now to FIG. 3, a cross-sectional top view of the catheter adapter of FIG. 1 is shown. As viewed from the top, the septum 50 generally comprises an hourglass shape. A proximal end 100 of the septum 50 is generally bell shaped and configured to form an interface 52 with the inner surface 26 of the catheter adapter 12. A distal end 102 of the septum 50 is similarly configured to form an interface 52 with the inner surface 26 of the catheter adapter 12. However, the distal end 102 of the septum 50 further comprises the docking portion 70 of the septum 50, as discussed in detail above. A middle portion 104 of the septum 50 thins thereby forming an expansion void 56 on either side of the middle portion 104 between the septum 50 and the inner surface 26 of the catheter adapter 12. The middle portion 104 of the septum 50 is generally located directly under the flow control button 90. As such, when the flow control button 90 is depressed, the middle portion 104 of the septum is actuated.

The middle portion 104 of the septum 50 further comprises a slit 60. The slit 60 is a physical opening through the septum 50 providing a pathway through the septum 50 whereby a fluid may move through the septum 50. The septum 50 is further configured such that the slit 60 is biased in a closed position, as illustrated. The slit 60 may be biased to an open position by depressing the flow control button 90 or forcing a probe through the slit 60 via the docking portion 70 of the septum 50, as discussed above. As the slit 60 is biased to an open position, the middle portion 104 of the septum 50 divides into two halves 64, 66, each half expanding radially outward into the provided expansion void 56. This process is discussed in further detail below in connection with FIG. 7 below.

Figure 4:
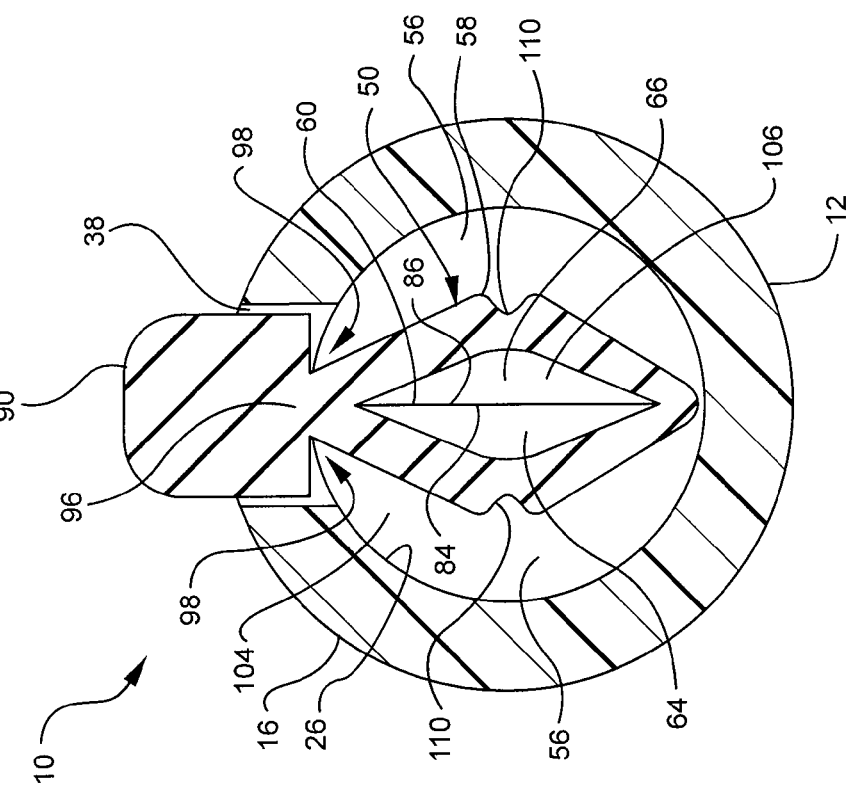
FIG. 4 is a cross-sectional view of the catheter assembly of FIG. 3 in a closed state.

Referring now to FIG. 4, a cross-sectional front view of the catheter of FIG. 3 is shown. The septum 50 further includes a crease 110. The crease 110 comprises a linear score on the outer surface 58 of the septum 50 and runs generally parallel to the body of the catheter adapter 16. The crease 110 is positioned at the apex of the middle portion 104 so as to run horizontally along the middle portion 104. The crease 110 is characterized as a thinned region of the outer surface 58 of the septum 50. The crease 110 weakens the structural integrity of the middle portion 104 wall thereby increasing the flexibility of the thinned region of the septum 50. As such, the crease 110 facilitates the middle portion 104 to bend towards the inner surface 26 of the catheter adapter 12 when the flow control button 90 is depressed. In this manner, a user may depress the button 90 and actuate the septum 50 wherein the outer surface 58 of the septum 50 bends outwardly towards the inner surface 26 of the catheter adapter 12.

The septum 50 further comprises an inner membrane 106. The inner membrane comprises a first half 64 and a second half 66, each half being separated by the slit 60. The inner membrane 106 is comprised of the same material as the remainder of the septum 50 and may comprise any thickness necessary to prevent unwanted passage of a fluid through the septum 50. The first and second halves 64, 66 of the inner membrane 106 further comprise a sealing surface 84, 86, respectively. The inner membrane 106 is configured such that the sealing surfaces 84, 86 of the first and second halves 64, 66 maintain contact with one another thereby forming a physical barrier preventing a fluid from passing through the septum 50. The sealing surfaces 84, 86 may be further modified to include complimentary surface designs. As such, the sealing surfaces 84, 86 may interlock or otherwise combine to further prevent the passage of fluid through the septum 50.

As previously discussed, a user may depress the flow control button 90 to actuate the septum 50. As the crease 110 of the septum 50 bends outwardly towards the inner surface 26 of the catheter adapter 12, the attached first and second halves 64, 66 of the inner membrane 106 are likewise pulled outwardly towards the inner surface 26 of the catheter adapter 12. As such, the sealing surfaces 84, 86 of the inner membrane 106 are drawn apart thereby opening the slit 60 of the septum 50 and enlarging the pathway through the septum 50.

A portion of the material of the septum 50 may be removed to form a notch 98 near the underside of the flow control button 90. The notch 98 may be provided to further ensure that the downward force of the depressed button 90 is focused on the slit 60 of the septum 50. In this manner, the downward force of the depressed button 90 is evenly distributed on the slit 60 thereby equally biasing each crease 110 of the middle portion 106 to bend outwardly towards the inner surface of catheter adapter 12, as previously described.

Figure 5:
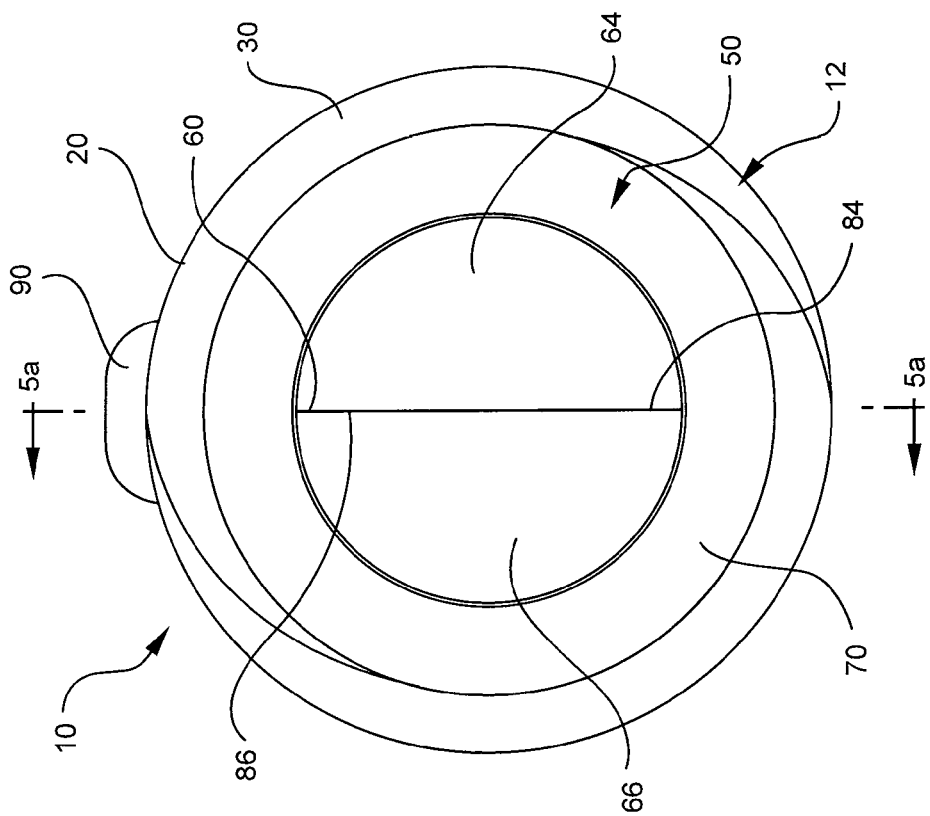
FIG. 5 is a perspective rear view of the catheter assembly of FIG. 3 in a closed state.

Referring now to FIG. 5, a perspective rear view of the catheter assembly 10 of FIG. 3 is shown. From the proximal end 20 of the catheter assembly 10, the first and second halves 64, 66 of the inner membrane 106 may be observed. As previously discussed, the proximal end 20 of the catheter adapter 12 may be modified to include a set of threads 30 or another feature for facilitating adapters or other components of an infusion system.

Figure 5A:
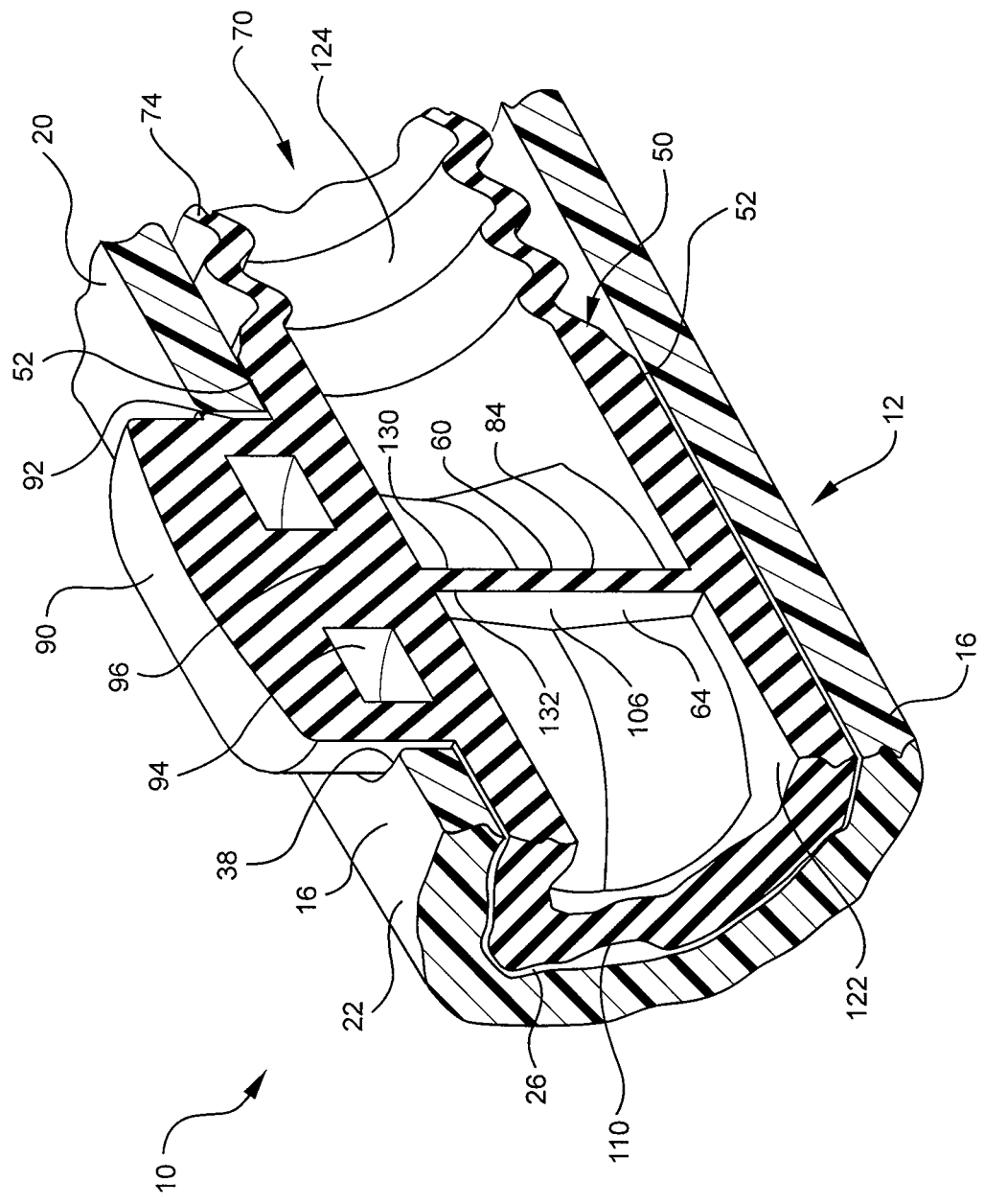
FIG. 5a is a cross-sectional view of the catheter assembly of FIG. 2 in a closed state.

Referring now to FIG. 5a, a cross-sectional view of the catheter assembly of FIG. 3 is shown in a closed state. The inner membrane 106 may be positioned within the lumen of the septum 50 so as to divide the septum 50 into a first chamber 122 and a second chamber 124. The first chamber 122 is generally defined as the enclosed space spanning between the tip 40 of the catheter 14 and the distal side 132 of the inner membrane 106. The second chamber 124 is generally defined as the enclosed space spanning between the proximal side 130 of the inner membrane 106 and the threads 30 of the catheter assembly 10. When the inner membrane 106 is in a closed state, as illustrated, a fluid may be contained within the first chamber 122 while the second chamber 124 remains isolated from the fluid within the first chamber 122. Conversely, a fluid may be contained within the second chamber 124 while the first chamber 122 remains isolated from the fluid within the second chamber 124. In this manner, a user may control the flow of a fluid through the septum 50 by controlling the open or close state of the inner membrane 106 of the septum 50.

Figure 6:
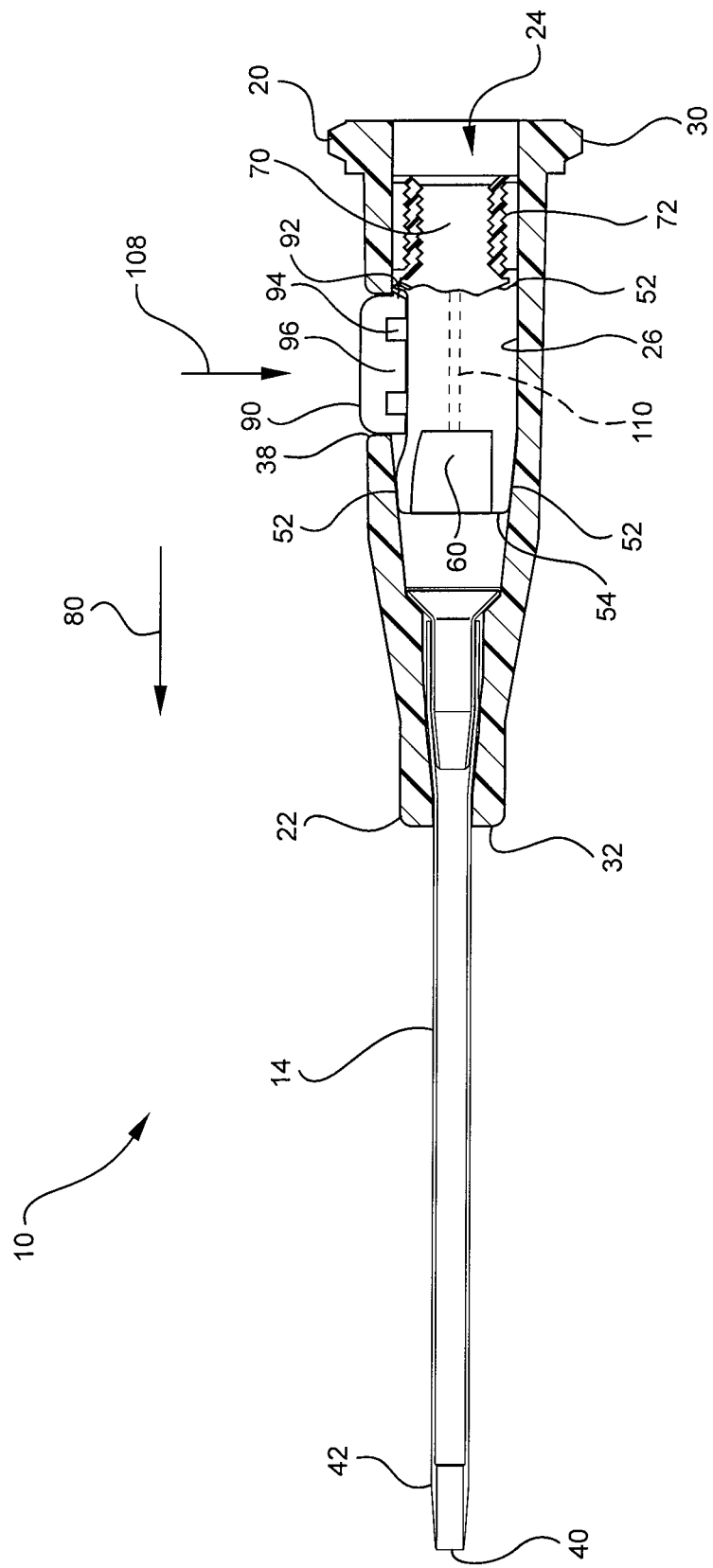
FIG. 6 is a cross-sectional side view of the catheter assembly of FIG. 1 in an opened state.
Figure 7:
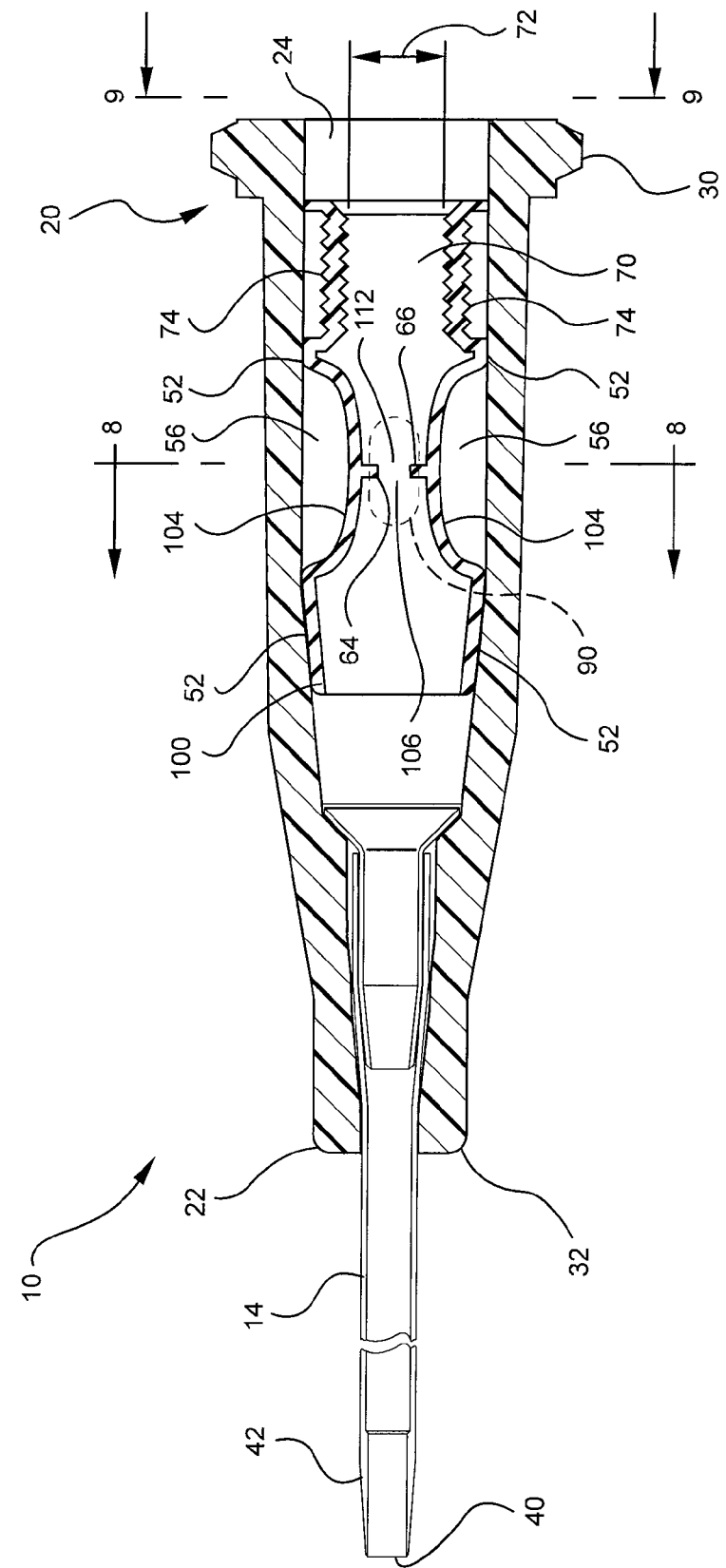
FIG. 7 is a cross-sectional top view of the catheter assembly of FIG. 1 in an opened state.

Referring now to FIG. 6, a cross-section side view of the catheter of FIG. 1 is shown in an opened state. The septum 50 may be opened by one of two methods. The septum 50 may be opened by inserting a probe into the docking portion 70 of the septum 50 and advancing the probe in a forward direction 80 such that the probe bypasses the inner membrane 106 of the septum 50, as previously described. Additionally, the septum 50 may be opened by depressing the flow control button 90, as illustrated. As the button 90 is depressed, the middle section 96 exerts a downward 108 force on the middle portion 104 of the septum 50. As the middle portion 104 is depressed in a downward 108 direction, the crease 110 of the middle portion 104 bends outwardly towards the inner surface 26 of the catheter adapter 12, as shown in FIG. 7. With continued reference to FIGS. 6 and 7, as the middle portion 104 bends outwardly into the expansion void 56, the first and second halves 64, 66 of the inner membrane 106 are separated thereby exposing a pathway 112 through the inner membrane 106.

A catch 92 may also be provided as part of the flow control button 90. A catch 92 may be positioned such that when the button 90 is depressed, the catch 92 passes through the window 38 and into the lumen 24 of the catheter adapter body 16. Once within the lumen 24, the catch 92 compatibly engages the inner surface 26 of the catheter adapter body 16 thereby holding the button 90 in a depressed position, as illustrated. The catch 92 may be disengaged from the inner surface 26 of the catheter adapter by simultaneously depressing the button 90 and biasing the button 90 in a forward direction 80, thereafter releasing the button 90 to a relaxed position.

Figure 8:
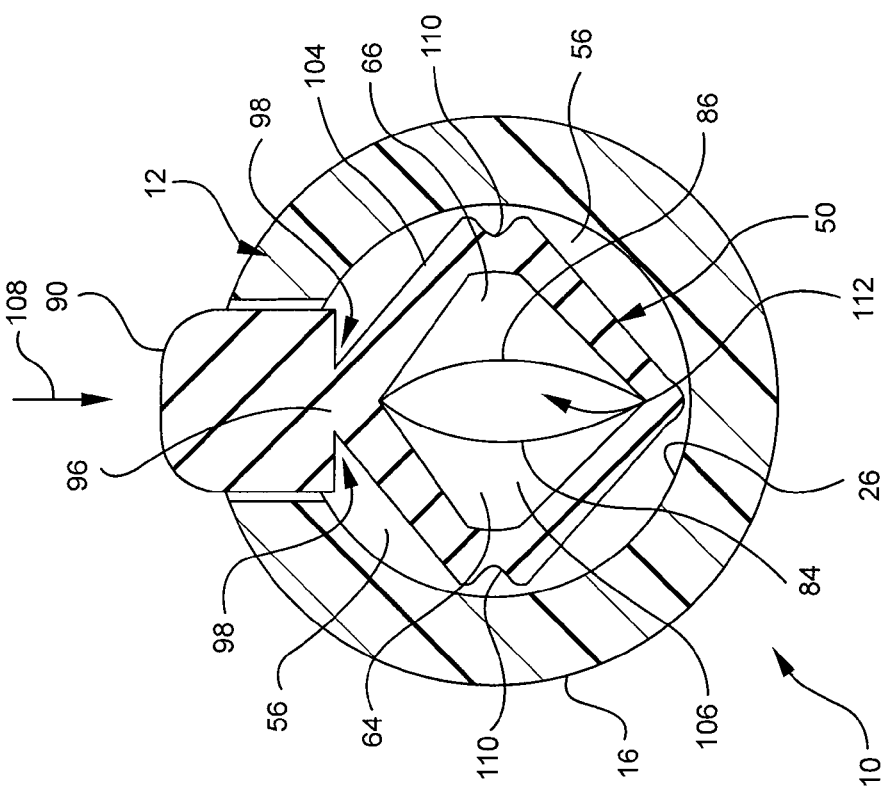
FIG. 8 is a cross-sectional view of the catheter assembly of FIG. 7 in an opened stated.

Referring now to FIG. 8, a cross-sectional front view of the catheter assembly of FIG. 7 is shown in an opened state. Again, as the flow control button 90 is depressed, the middle section 96 of the button 90 exerts a downward 108 force on the middle portion 104 of the septum 50. The crease 110 of the middle portion 104 bends outwardly towards the inner surface 26 of the catheter adapter 12. As such, the first and second halves 64, 66 of the inner membrane 106 are separated to expose a pathway 112 through the inner membrane 106.

Figure 9:
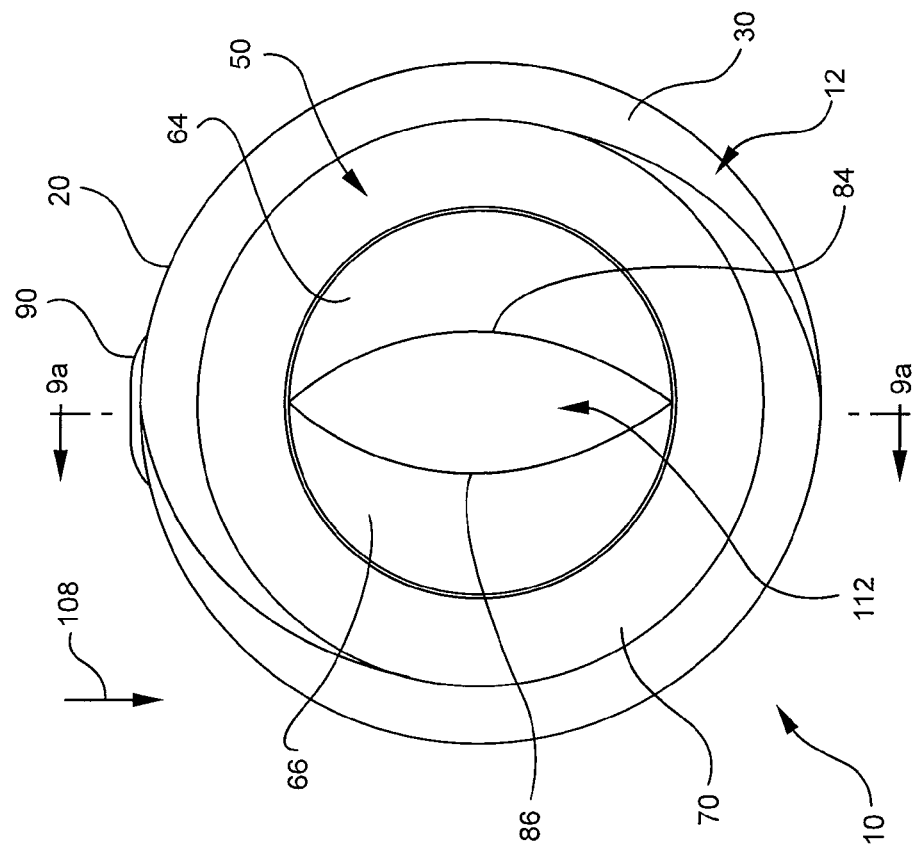
FIG. 9 is a perspective rear view of the catheter assembly of FIG. 7 in an opened state.

Referring now to FIG. 9, a perspective rear view of the catheter assembly of FIG. 7 is shown in an opened state. From the proximal end 20 of the catheter assembly 10, the first and second halves 64, 66 of the inner membrane 106 may be observed. Once actuated by depressing the flow control button 90, the first and second halves 64, 66 are separated revealing a pathway 112 through the septum 50. By depressing the flow control button 90, the first and second halves 64, 66 of the septum 50 are biased outwardly and separated in a manner as illustrated.

Figure 9A:
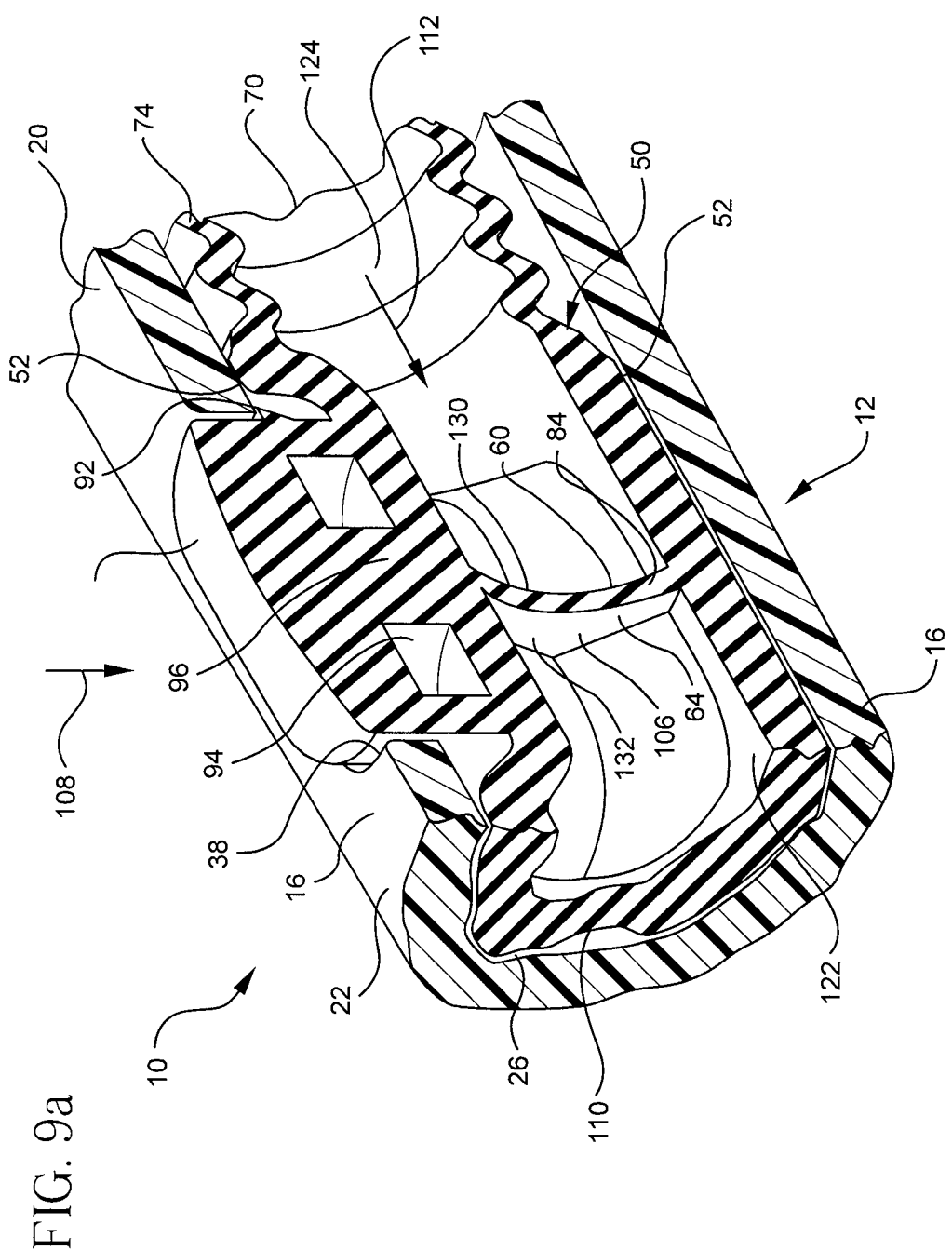
FIG. 9a is a cross-sectional view of the catheter assembly of FIG. 6 in an open state.

Referring now to FIG. 9a, a cross-sectional view of the catheter assembly of FIG. 7 is shown in an opened state. The first and second halves 64, 66 of the inner membrane 106 of the septum 50 are biased outwardly towards the inner surface 26 as the flow control button 90 is depressed. Specifically, a middle section 96 of the flow control button 94 is provided to exert a focused, downward 108 force on inner membrane 106 of the septum 50. The downward 108 force causes the first and second halves 64, 66 of the membrane to relax outwardly and separate from one another revealing a pathway 112 through the septum 50.

Figure 10:
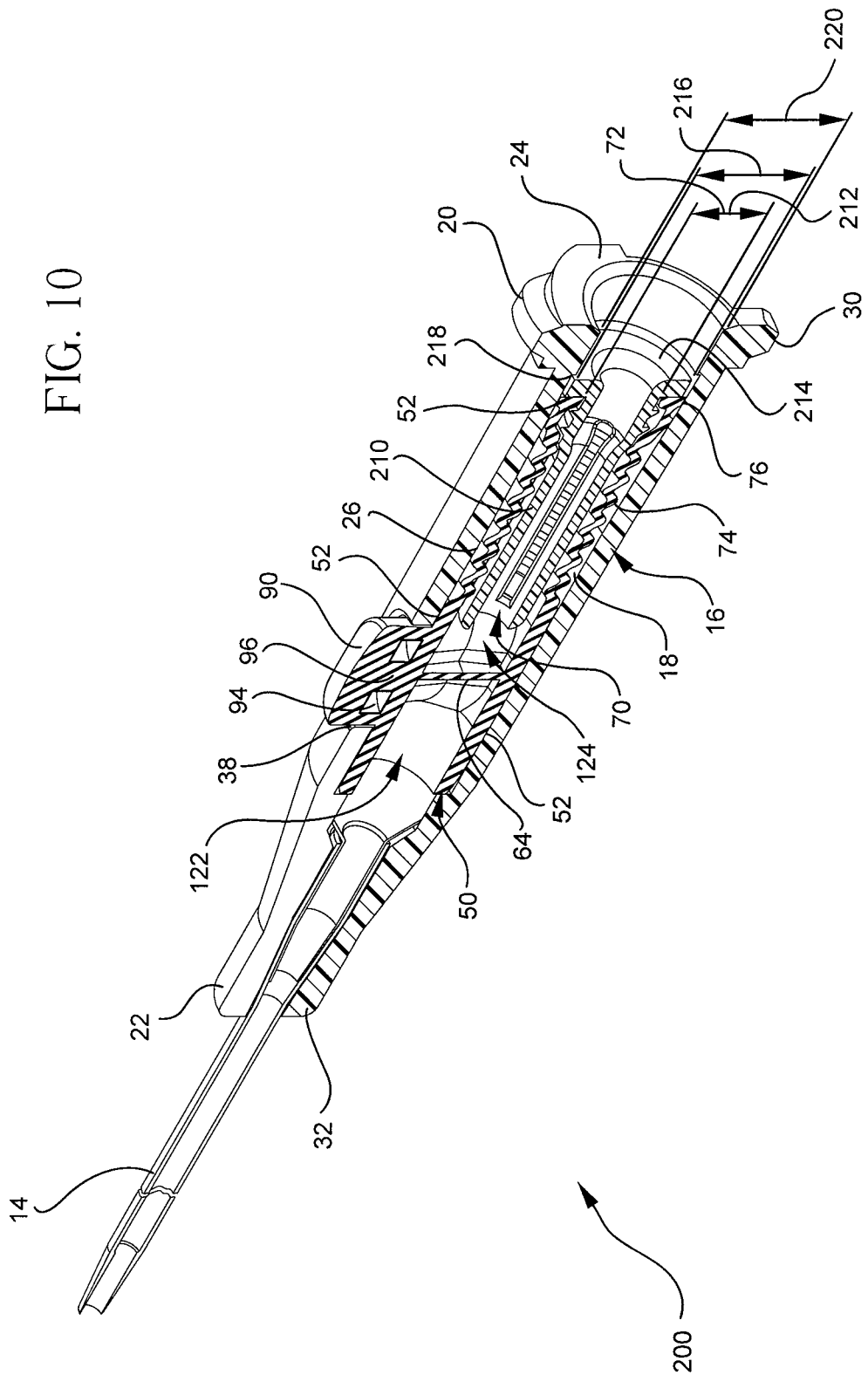
FIG. 10 is a cross-sectional side view of a catheter assembly in a closed state, the catheter assembly including an actuator.

Referring now to FIG. 10, a cross-sectional side view of a second embodiment of a catheter assembly 200 is show. In this embodiment, the catheter assembly is modified to include an actuator 210. The actuator 210 is generally tubular with an outer diameter 212 selected to slidably nest within the docking portion 70 of the septum 50. The actuator 210 further includes a flange 214 comprising the proximal end of the actuator 210. The flange 214 comprises an outer diameter that is greater than the inner diameter 72 of the docking portion 70 of the septum 50. As such, the flange 214 is prevented from moving beyond the proximal end 76 of the docking portion 70 of the septum 50. The actuator 210 may be further retained within the catheter adapter body 16 by modifying the catheter adapter body 16 to include an inner compartment 18. The inner compartment 18 comprises actuator stop 218 to prevent the actuator 210 from exiting the catheter adapter 12 through the proximal end 20 opening. The actuator stop 218 comprises an annular ridge formed on the inner surface 26 of the catheter adapter body 16. The actuator stop 218 further comprises an inner diameter 220 selected to be less than the outer diameter 216 of the flange 214 of the actuator 210. As such, the flange 214 is positioned within the lumen 24 of the catheter adapter body 16, between the proximal end 76 of the docking portion 70 and the actuator stop 218 as formed on the inner surface 26 of the catheter adapter body 16.

A variety of variations are possible with the current embodiment. For example, in one embodiment the catheter adapter does not comprise an actuator stop 218, but rather the actuator 210 is fastened to the proximal end 76 of the docking portion 70 via an adhesive. Alternatively, the actuator 210 may be fastened to the proximal end 76 of the docking portion 70 by molding the proximal end 76 to include an annular channel for receiving the flange 214 of the actuator 210. In another embodiment, a catheter adapter is configured to include the actuator stop 218 but excludes the actuator 210. Rather, the actuator stop 218 forms an interface with the proximal end 76 of the docking portion 70. As such, the ribbed section 74 of the docking portion 70 may be partially compressed within the inner compartment 18 and held in a partially compressed state via friction contact with the actuator stop 218.

Figure 11:
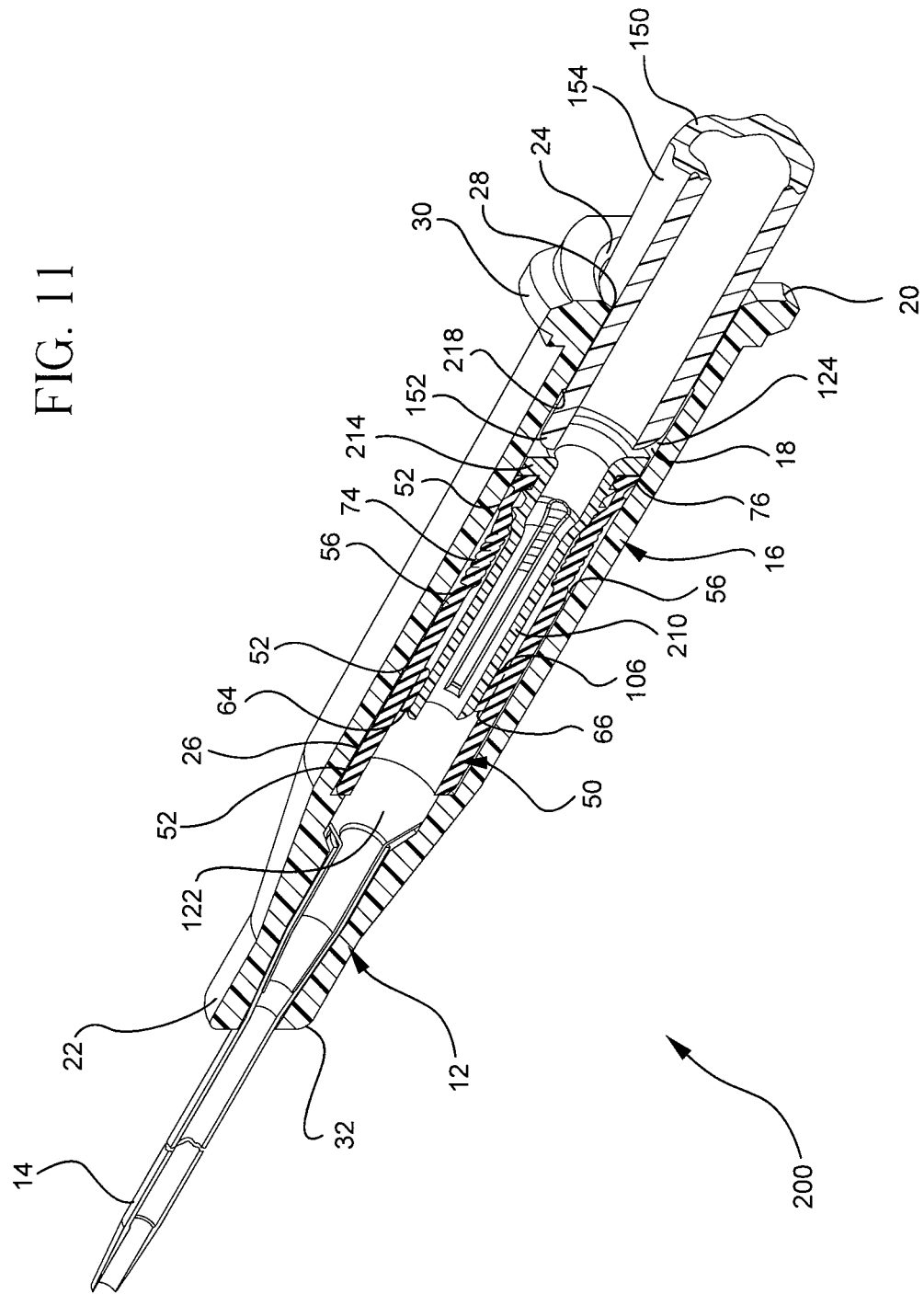
FIG. 11 is a cross-sectional top view of the catheter assembly of FIG. 10 as actuated by a probe.

Referring now to FIG. 11, a cross-sectional top view of the catheter assembly 200 of FIG. 10 is shown, as actuated by a probe 150. The septum 50 of the catheter assembly 200 may be actuated either by depressing the flow control button 90, as previously discussed, or by inserting a probe 150 into the opening of the proximal end 20 of the catheter adapter 12. The septum 50 is actuated as the tip 152 of the probe 150 contacts the flange 214 and advances the actuator 210 through the septum 50. The actuator 210 biases the first and second halves 64, 66 of the inner membrane 106 outwardly towards the inner surface 26 of the catheter adapter body 16. As such, the actuator 210 creates a passage 112 through the septum 50.

The probe 150 may be configured to interact with the inner surface 28 of the proximal end 20 of the catheter adapter 12. For example, the outer surface 154 of the probe 150 may be configured to taper inwardly such that as the probe 150 is inserted into the lumen 24 of the catheter adapter 12, the outer surface 154 of the probe 150 contacts the inner surface 28 of the proximal end 20 of the catheter adapter 12. As such, the probe 150 may be wedged within the proximal end 20 of the catheter adapter 12 and held in place via friction between the outer surface 154 of the probe 150 and the inner surface 28 of the proximal end 20 of the catheter adapter 12.

Figure 12:
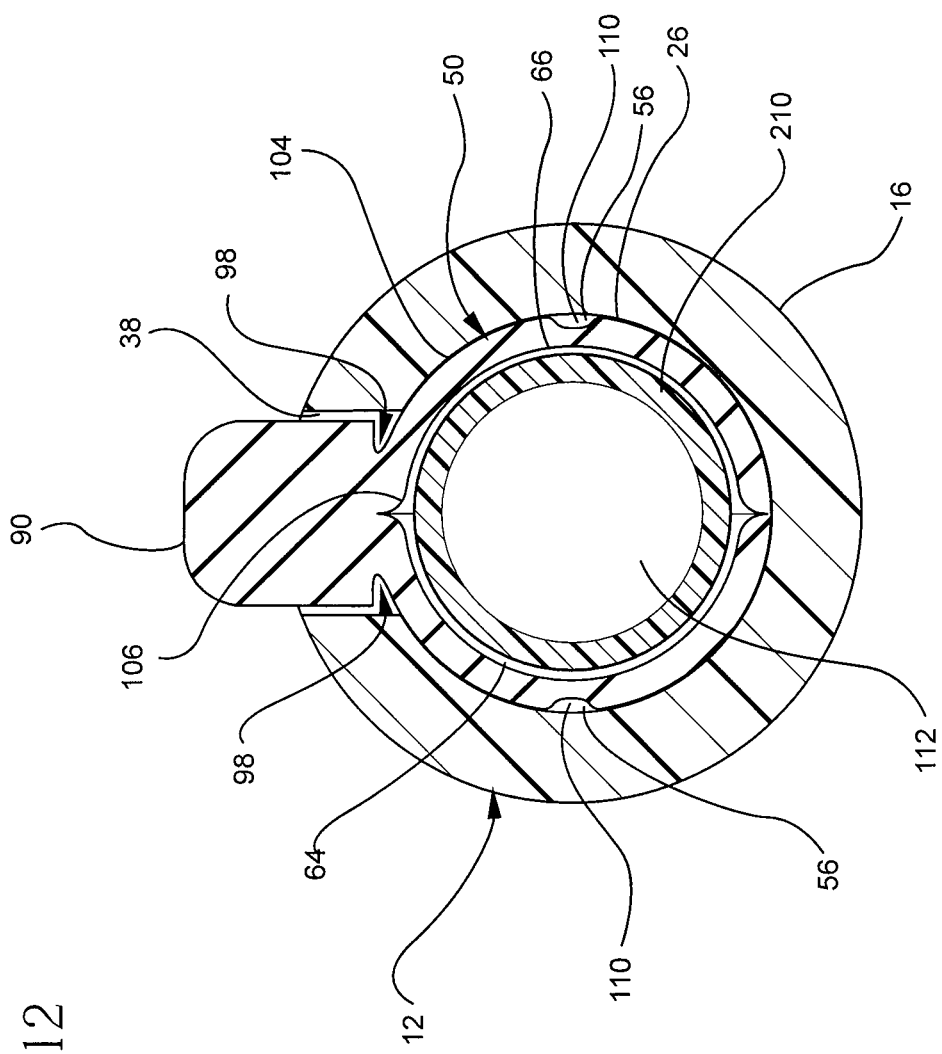
FIG. 12 is a cross-sectional front view of the catheter assembly of FIG. 11.

Referring now to FIG. 12, a cross-section front view of the catheter assembly of FIG. 11 is shown. As the probe 150 advances the actuator 210 through the first and second halves 64, 66 of the inner membrane 106, the first and second halves 64, 66 are biased outwardly towards the inner surface 26 of the catheter adapter body 16. As such, the actuator 210 provides a clear pathway 112 through the septum 50. The expansion void 56 provides sufficient clearance such that the middle portion 104 of the septum 50 may expand outwardly without contacting the inner surface 26 of the catheter adapter body 16.

Referring again to FIG. 11, as the probe 150 is removed from the proximal end 20 of the catheter assembly 200, the compressed ribbed section 74 of the septum 50 is released thereby returning the actuator 210 to the pre-actuated position as in FIG. 10. As the actuator 210 is returned to the pre-actuated position, the first and second halves 64, 66 of the septum 50 return to a closed position thereby reestablishing a first and second chamber 122, 124 as shown in FIGS. 5a and 10.

Figure 13:
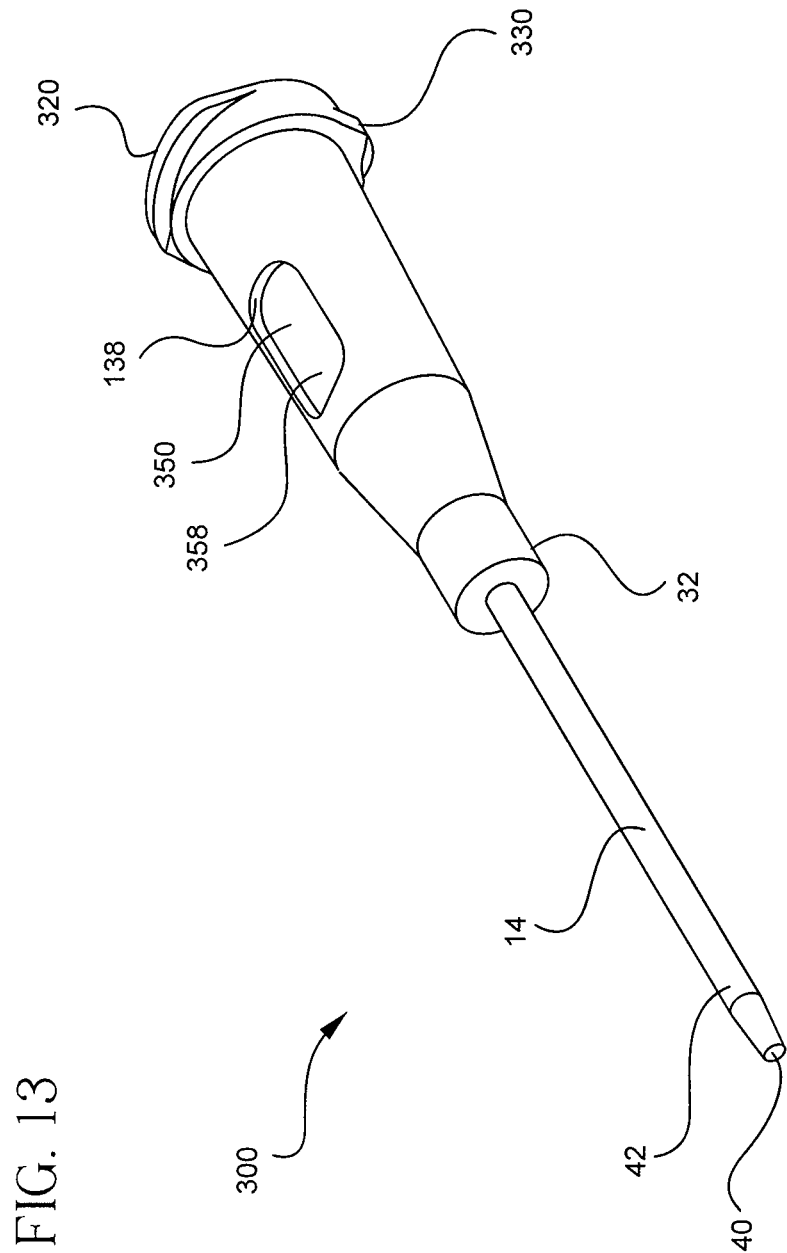
FIG. 13 is a perspective view of a catheter assembly with a rigid exoskeleton.

Referring now to FIG. 13, a third embodiment of a catheter assembly 300 is shown. The present embodiment comprises a catheter adapter body 312 and a catheter 14. The catheter 14 is comparable to the catheter 14 of the previous embodiment as described in connection with the previous figures. The catheter adapter body 312 comprises a rigid or semi-rigid material for encasing a flexible or semi-flexible septum 350. The catheter adapter body 312 generally comprises an outer shell or exoskeleton-like covering for the septum 350. The material of the catheter adapter body 312 is generally selected such that a set of threads 330 may be provided at the proximal end 320 of the catheter assembly 300. The material of the threads 330 must be sufficiently rigid such that a complementary set of threads may be coupled thereto. For example, a complementary set of threads may be incorporated into a component of an infusion system. As such, the component may be coupled to the catheter assembly 300 by engaging the threads of the component with the threads of the catheter assembly 330. The catheter adapter body 312 further comprises a window 138 through which a user may contact the outer surface 358 of the septum 350.

Figure 13A:
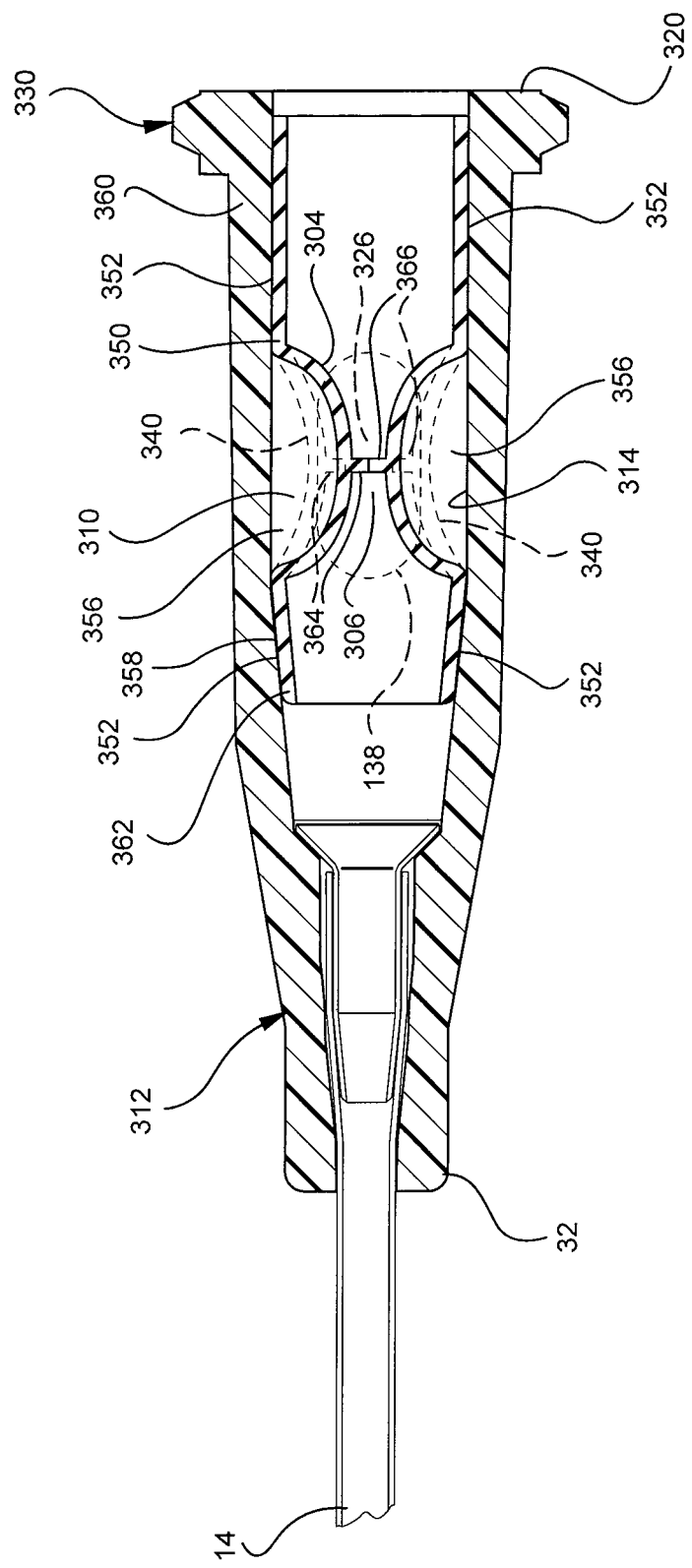
FIG. 13a is a cross-sectional top view of the catheter assembly of FIG. 13.

Referring now to FIG. 13a, a cross-sectional top view of the catheter assembly 300 of FIG. 13 is shown. The septum 350 comprises a flexible material similar to that of the septum 50 described in connection with the previous embodiments. The material of the septum 350 is generally flexible and may comprise any flexible or semi-flexible polymer material such as nylon, Teflon, or silicone. The septum 350 comprises a proximal 360 and a distal end 362. The septum 350 is molded to compatibly fit within the lumen 310 of the catheter adapter body 312. As such, the outer surface 358 of the septum 350 forms an interface 352 with the inner surface 314 of the catheter adapter body 312. The interface 352 creates a fluidtight seal between the septum 350 and the inner surface 314 of the catheter adapter 312. As such, a fluid may pass through the catheter assembly 300 without leaking into the lumen 310 of the catheter adapter 312.

The window 138 is positioned such that a user may depress the outer surface 358 of the septum 350 at a location adjacent to the middle portion 304 of the septum 350. One or more windows 138 may be provided. For example, a second window may be provided for the catheter assembly 300 at a location 180 degrees from the provided window 138. As such, a user may contact and pinch the septum 350 from both an upper and a lower side to actuate the septum 350.

The septum 350 may be actuated by depressing the outer surface 358 of the septum 350 adjacent to the middle portion 304 of the septum 350. As the outer surface 358 is depressed, the middle portion 304 of the septum 350 is biased outwardly into an expansion void 356. The expansion void 356 comprises a physical gap between the middle portion 304 of the septum 350 and the inner surface 314 of the catheter adapter body 312. As the middle portion 304 of the septum 350 is biased outwardly into an open position 340, the first and second halves 364, 366 of the inner membrane 306 are separated to provide a pathway 326 through the septum 350. As with the previous embodiments, the septum 350 may also be actuated by advancing a probe through the inner membrane 306 to provide a pathway 326.

Figure 14:
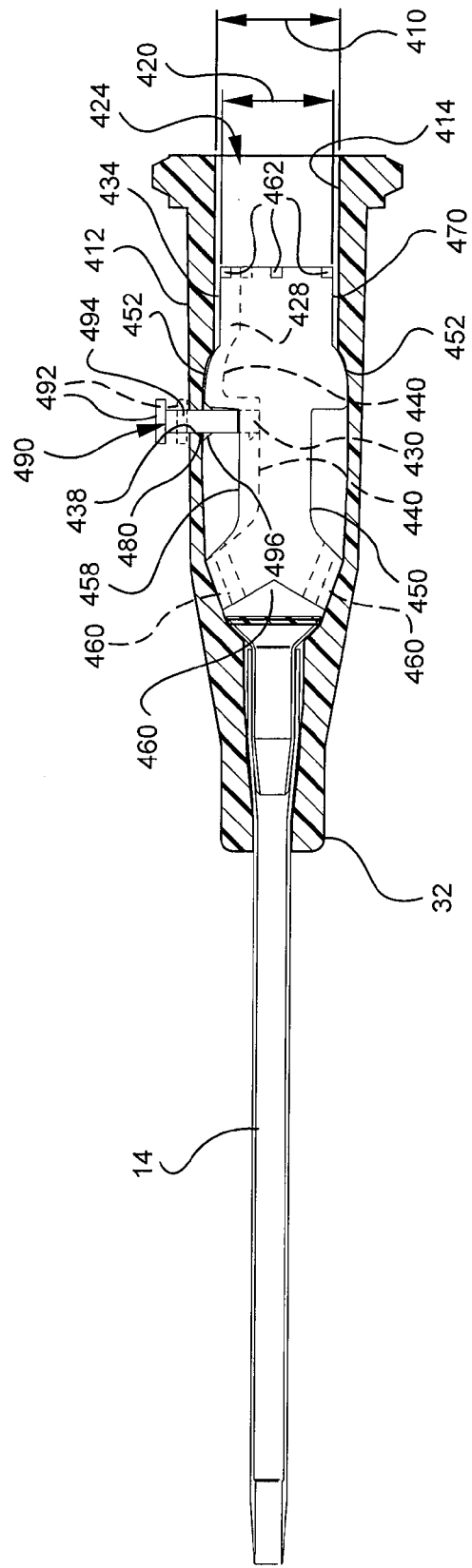
FIG. 14 is a cross-sectional side view of a catheter assembly with an obstructing septum.

Referring now to FIG. 14, a cross-sectional side view of a final embodiment of a catheter assembly 400 is shown. The present embodiment comprises a catheter adapter body 412 and a catheter 14. The catheter 14 is comparable to the catheter 14 of the previous embodiments as described in connection with the previous figures. The catheter adapter body 412 is generally rigid and generally comparable to the catheter adapter body 12 of the embodiment described in connection with FIGS. 1-12, above. However, the present catheter adapter body 412 comprises a window 438 that is configured to house a flow control button 490. The flow control button 490 differs from the previous flow control button 90 in that the current flow control button 490 does not comprise an extended portion of the septum. Rather, the flow control button 490 comprises a contact surface 492 connected to a shaft 494 for depressing an outer surface 458 of the septum 450. However, the septum 450 could also comprise an extension of the septum 450 in place of the flow control button 490. For example, the septum extension could be exposed whereby a user could depress the septum extension and actuate the septum 450 in a manner similar to being actuated via the button 490.

In either embodiment, a sealing mechanism 480 is required to prevent a fluid from leaking through the window 438 of the catheter assembly 400. The sealing mechanism 480 may include a system of gaskets, seals, o-rings or other appropriate devices for preventing leakage. The shaft 494 further comprises a system of barbs 496. The system of barbs 496 extends laterally from the outer surface of the shaft 494. As such, the system of barbs 496 binds on the inner surface 414 of the catheter adapter body 412 and prevent the shaft from exiting through the window 438.

The septum 450 is positioned within the lumen 424 of the catheter adapter 312 and generally comprises a flexible or semi-flexible material such as those previously described. Unlike the previous septum 50, 350, the current septum 450 is generally solid or comprises an enclosed, inaccessible lumen. Rather than providing a pathway through the catheter assembly, the current septum 450 is provided to obstruct the pathway through the lumen 424 of the catheter adapter body 412. This obstruction is due to a fluidtight interface 452 between the outer surface 458 of the septum 450 and the inner surface 414 of the catheter adapter body 412. The current septum 450 is actuated as the button 490 is depressed 430 thereby depressing the outer surface 458 of the septum 450 to an opened position 440. As such, the interface 452 is displaced to reveal a pathway 428 between the septum 450 and the inner surface of the catheter adapter body 412. The septum 450 further comprises flow channels 460 to permit a fluid to by pass the septum 450 and flow through the catheter assembly 400.

The proximal end 470 of the septum 450 comprises an outer diameter 420 that is less than the inner diameter 410 of the catheter adapter body 412. As such, a fluid may flow between the outer surface 434 of the proximal end 470 and the inner surface 414 of the catheter adapter body 412. However, a fluid is prevented from bypassing the septum 450 due to the interface 452, as previously discussed. The proximal end 470 of the septum 450 may be further configured to comprise flow channels 462. These flow channels 462 permit a fluid from a probe to bypass the proximal end 470 of the septum 450 when the catheter assembly 400 is actuation with a probe, as shown in FIG. 15, below.

Figure 15:
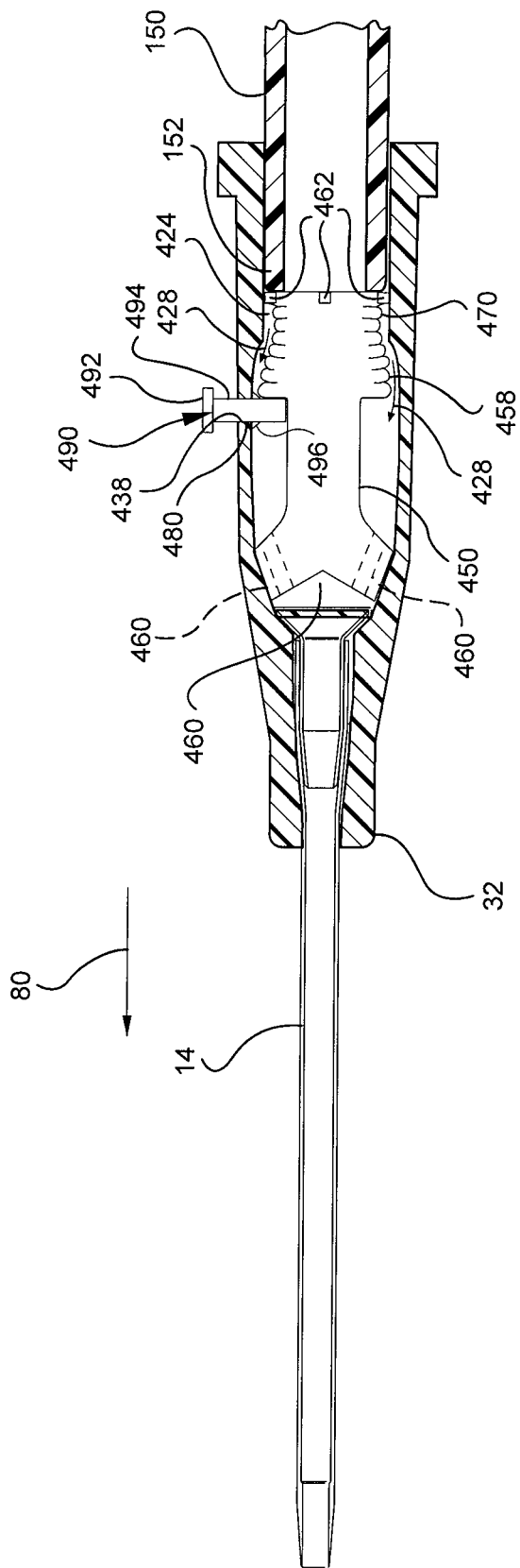
FIG. 15 is a cross-sectional side view of the catheter assembly of FIG. 14 as actuated by a probe.

Referring now to FIG. 15, a cross-sectional side view of the catheter assembly 400 of FIG. 14 is shown as actuated by a probe 150. The septum 450 is compressed in a forward 80 direction as the tip 152 of the probe 150 is advanced within the lumen 424 of the catheter adapter body 412. As the proximal end 470 of the septum 450 is compressed by the probe 150, the interface 452 is disrupted such that a pathway 428 is provided between the outer surface 458 of the septum and the inner surface 414 of the catheter adapter body 412. The flow channels 462 of the proximal end 470 of the septum 450 are provided to prevent a fluidtight interface between the tip 152 of the probe 150 and the septum 450. As provided, the flow channels 462 permit a fluid to flow past the proximal end 470 of the septum 450 and continue though the pathway 428 and the remainder of the catheter assembly 400. Additional features and adaptations, consistent with the previously disclosed embodiments may further be implemented with catheter assembly 400, within the scope of the current invention.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter adapter comprising:
   a catheter adapter body having a proximal end and a distal end and forming a lumen, wherein the proximal end is configured to allow a separate device to be attached to the catheter adapter body, the catheter adapter having a window;
   a catheter that extends from the distal end of the catheter adapter body;
   a septum positioned within the lumen of the catheter adapter body, the septum comprising a slit that is biased in a closed position to prevent fluid flow through the lumen;
   a button contained within the window which when pressed causes the slit of the septum to open thereby creating a fluid pathway through the lumen;
   wherein a proximal end of the septum is configured to compress when a probe or actuator is inserted distally through the proximal end of the septum and through the slit, the insertion of the probe or actuator through the slit creating a fluid pathway through the lumen, and wherein, the compressed proximal end of the septum applies a recoil force against the probe or actuator while the probe or actuator is inserted through the slit to thereby reduce the force required to remove the probe or actuator from the slit.

2. The catheter adapter of claim 1, further comprising:
an actuator that is contained within the proximal end of the septum, the actuator being configured to be forced through the slit when a probe is inserted through the proximal end of the catheter adapter body.

3. The catheter adapter of claim 2, wherein the actuator is coupled to the proximal end of the septum.

4. The catheter adapter of claim 2, wherein the lumen includes an actuator stop that limits proximal movement of the actuator.

5. The catheter adapter of claim 1, wherein the button comprises a portion of the septum.

6. The catheter adapter of claim 1, wherein the button includes a wedged extension that catches on an edge of the window when the button is compressed thereby retaining the button in a compressed position.

7. The catheter adapter of claim 1, wherein the button comprises one or more channels that are formed perpendicular to a length of the button.

8. The catheter adapter of claim 1, wherein the proximal end of the septum comprises a series of raised, annular ridges.

9. The catheter adapter of claim 1, wherein the septum includes a crease comprising a thinned region of an outer surface of the septum that runs generally parallel to a length of the catheter adapter body.

10. The catheter adapter of claim 1, wherein the septum includes a notch that is positioned under the button.

11. A catheter adapter comprising:
a catheter adapter body having a proximal end and a distal end and forming a lumen, wherein the proximal end is configured to allow a separate device to be attached to the catheter adapter body, the catheter adapter body having a window;
catheter that extends from the distal end of the catheter adapter body;
a septum positioned within the lumen of the catheter adapter body, the septum comprising a slit that is biased in a closed position to prevent fluid flow through the lumen;
an actuator contained within a proximal portion of the septum, the actuator being configured to extend through the slit when a separate device is inserted into the proximal end of the catheter adapter body thereby creating a fluid pathway through the lumen; and
a button contained within the window which when pressed causes the slit of the septum to open thereby creating a fluid pathway through the lumen.

12. The catheter adapter of claim 11, wherein the proximal portion of the septum is configured to compress when the actuator extends through the slit and to retract to an uncompressed position when the separate device is removed from the proximal end of the catheter adapter body, the retraction to the uncompressed position retracting the actuator from within the slit thereby closing the fluid pathway.

13. The catheter adapter of claim 12, wherein the proximal portion of the septum comprises a series of raised, annular ridges.

14. The catheter adapter of claim 11, wherein the button comprises a portion of the septum.

15. The catheter adapter of claim 14, wherein the button includes one or more channels that are formed perpendicular to a length of the button.

16. The catheter adapter of claim 11, wherein the button includes a wedged extension that catches on an edge of the window when the button is compressed thereby retaining the button in a compressed position.

17. A catheter adapter comprising:
a catheter adapter body having a proximal end and a distal end and forming a lumen, wherein the proximal end is configured to allow a separate device to be attached to the catheter adapter body, the catheter adapter body having a window;
catheter that extends from the distal end of the catheter adapter body;
a septum positioned within the lumen of the catheter adapter body, the septum comprising a slit that is biased in a closed position to prevent fluid flow through the lumen, the septum having a proximal portion that is compressible;
an actuator coupled to the proximal portion of the septum, the actuator being configured to be forced through the slit when a separate device is inserted into the proximal end of the catheter adapter body thereby creating a fluid pathway through the lumen, wherein the forcing of the actuator through the slit causes the proximal portion of the septum to be compressed, and wherein, once the separate device is retracted from the proximal end of the catheter body, the proximal portion of the septum returns to an uncompressed position thereby withdrawing the actuator from within the slit; and
a button contained within the window which when pressed causes the slit of the septum to open thereby creating a fluid pathway through the lumen.

18. The catheter adapter of claim 17, wherein the button includes a wedged extension that catches on an edge of the window when the button is compressed thereby retaining the button in a compressed position.

* * * * *